United States Patent
Curiel

(10) Patent No.: US 9,267,153 B2
(45) Date of Patent: Feb. 23, 2016

(54) PORCINE KNOB XENOTYPE CHIMERIC ADENOVIRAL VECTOR FOR DENDRITIC CELL INFECTION

(71) Applicant: Washington University, Saint Louis, MO (US)

(72) Inventor: David T Curiel, Saint Louis, MO (US)

(73) Assignee: Washington University, Saint Louis, MO (US)

( * ) Notice: Subject to any disclaimer, the term of this patent is extended or adjusted under 35 U.S.C. 154(b) by 0 days.

(21) Appl. No.: 14/365,957

(22) PCT Filed: Dec. 14, 2012

(86) PCT No.: PCT/US2012/069884
§ 371 (c)(1),
(2) Date: Jun. 16, 2014

(87) PCT Pub. No.: WO2013/090806
PCT Pub. Date: Jun. 20, 2013

(65) Prior Publication Data
US 2015/0017195 A1    Jan. 15, 2015

Related U.S. Application Data

(60) Provisional application No. 61/576,116, filed on Dec. 15, 2011.

(51) Int. Cl.
*C12N 15/86* (2006.01)
*A61K 39/00* (2006.01)

(52) U.S. Cl.
CPC .......... *C12N 15/86* (2013.01); *A61K 2039/5256* (2013.01); *C12N 2710/10041* (2013.01); *C12N 2710/10322* (2013.01); *C12N 2710/10343* (2013.01); *C12N 2810/6018* (2013.01)

(58) Field of Classification Search
None
See application file for complete search history.

(56) References Cited

U.S. PATENT DOCUMENTS

| | | | |
|---|---|---|---|
| 7,232,899 | B2 | 6/2007 | Von Seggern et al. |
| 7,741,099 | B2 | 6/2010 | Havenga |
| 8,415,118 | B2 | 4/2013 | Huang et al. |
| 8,470,310 | B2 | 6/2013 | Roy et al. |
| 8,871,515 | B2 | 10/2014 | Brennan et al. |
| 8,871,905 | B2 | 10/2014 | Holmes et al. |
| 2002/0193327 | A1 | 12/2002 | Nemerow et al. |
| 2003/0124091 | A1 | 7/2003 | Tuse et al. |
| 2006/0062764 | A1 | 3/2006 | Police et al. |
| 2006/0228334 | A1 | 10/2006 | Rosa-Calatrava et al. |
| 2010/0083391 | A1* | 4/2010 | Hamilton et al. ............ 800/10 |
| 2011/0158957 | A1 | 6/2011 | Bonini et al. |
| 2015/0017195 | A1* | 1/2015 | Curiel ....................... 424/186.1 |

FOREIGN PATENT DOCUMENTS

EP   PCT/EP2002/001257 A2   8/2002

OTHER PUBLICATIONS

Guardado-Calvo et al. (Journal of Virology. Oct. 2010; 84 (20): 10558-10568).*
Dai et al. (Journal of Immunology. 2005; 175: 2974-2981).*
Krasnykh et al. (Journal of Virology. Mar. 1998; 72 (3): 1844-1852).*
van de Ven et al. (Journal of Immunotherapy. 2009; 32: 895-906).*
Sequence alignment of SEQ ID No. 1 with Geneseq database access No. AXX10328 in CN101579527 by Ji et al.*
Sequence alignment of SEQ ID No. 2 with Geneseq database access No. AAE13474 in WO200177302 by Vie et al.*
Sequence alignment of SEQ ID No. 3 with Geneseq database access No. AAR66538 in WO9426903 by Melief et al.*
Sequence alignment of SEQ ID No. 4 with Geneseq database access No. ATM59919 in US20082199947 by Linette et al.*
Sequence alignment of SEQ ID No. 5 with Geneseq database access No. ATM59920 in US20082199947 by Linette et al.*
Altamirano, M.M., et al., Ligand-independent assembly of recombinant human CD1 by using oxidative refolding chromatography. Proc. Nat'l Acad. Sci. 98 (6): 3288-3293, Mar. 13, 2001. USA.
Belousova, N., et al, Modulation of adenovirus vector tropism via incorporation of polypeptide ligands into the fiber protein. J. Virol. 76 (6): 8621-31, Sep. 2002. USA.
Bergelson, J.M., et al. Isolation of a common receptor for Coxsackie B viruses and adenoviruses 2 and 5. Science. 275: 1320-3, 28 Feb. 1997. Washington DC, USA.
Cella, M., et al., Maturation, activation, and protection of dendritic cells induced by double-stranded RNA. J. Exp. Med. 189 (5): 821-829, Mar. 1, 1999. New York, NY USA.
Chartier, C., et al., Efficient generation of recombinant adenovirus vectors by homologous recombination in *Escherichia coli*. J. Virol. 70(7): 4805-10, Jul. 1996.
Deutscher, S.L., et al., Mechanism of galactosylation in the Golgi apparatus. A Chinese hamster ovary cell mutant deficient in translocation of UDP-galactose across Golgi vesicle membranes. J. Biol. Chem. 261 (1): 96-100, Jan. 5, 1986. USA.
Dwek, R.A., Glycobiology: Toward Understanding the Function of Sugars. Chem. Rev. 96 (2): 683-720, 1996.
Elbein, A.D., et al., Swainsonine: an inhibitor of glycoprotein processing. Proc. Natl. Acad. Sci. USA. 78 (12): 7393-7, Dec. 1981.
Fong, L., et al., Dendritic cells in cancer immunotherapy. Annu. Rev. Immunol. 18: 245-273, 2000.
Glasgow, J.N., et al., An adenovirus vector with a chimeric fiber derived from canine adenovirus type 2 displays novel tropism. Virol. 324: 103-16, 2004.
Gong, J., et al., Induction of antitumor activity by immunization with fusions of dendritic and carcinoma cells. Nat. Med. 3(11): 558-561, May 1997.
Guardado-Calvo, P., Llamas-Saiz, A.L., et al., Crystallization of the head and galectin-like domains of porcine adenovirus isolate NADC-1 fibre. Acta. Crystallogr. Sect. F Struct. Biol. Cryst. Commun. Nov. 1, 2009;65(Pt 11):1149-52.

(Continued)

*Primary Examiner* — Shanon A Foley
(74) *Attorney, Agent, or Firm* — Zackson Law, LLC; Saul L. Zackson

(57) ABSTRACT

Disclosed are methods of transforming dendritic cells with a chimeric adenovirus-5 (Ad5). A chimeric adenovirus includes a fiber comprising a tail, a shaft and a knob, wherein the knob is a porcine knob, and a nucleic acid comprising a promoter operably linked to a heterologous sequence encoding an antigen peptide.

18 Claims, 10 Drawing Sheets

(56) References Cited

OTHER PUBLICATIONS

Guardado-Calvo, P., Muñoz, E.M., et al., Crystallographic structure of porcine adenovirus type 4 fiber head and galectin domains. J. Virol. 84 (20): 10558-68, Oct. 2010.

Hartmann, G., et al., CpG DNA: a potent signal for growth, activation, and maturation of human dendritic cells. Proc. Natl. Acad. Sci. USA. 96: 9305-9310, 1999.

Krasnykh, V., Belousova, N., et al., Genetic targeting of an adenovirus vector via replacement of the fiber protein with the phage T4 fibritin. J. Virol. 75(9): 4176-83, May 2001.

Krasnykh, V., Dmitriev, I., et al., Characterization of an adenovirus vector containing a heterologous peptide epitope in the HI loop of the fiber knob. J. Virol. 72(3): 1844-52, Mar. 1998.

Krasnykh, V.N., Mikheeva, G.V., et al., Generation of recombinant adenovirus vectors with modified fibers for altering viral tropism. J. Virol. 70(10): 6839-46, Oct. 1996.

Kuan, S.F., et al., Inhibition of mucin glycosylation by aryl-N-acetyl-alpha-galactosaminides in human colon cancer cells. J. Biol. Chem. 264(32): 19271-7, Nov. 15, 1989.

Li, H., d'Anjou, M., Pharmacological significance of glycosylation in therapeutic proteins. Curr. Opin. Biotechnol. 20: 678-84, 2009.

Li, K. Fazekasova, H., et al., Expression of complement components, receptors and regulators by human dendritic cells. Mol. Immunol. 48: 1121-1127, 2011.

Maizel, J.V., et al., The polypeptides of adenovirus. I. Evidence for multiple protein components in the virion and a comparison of types 2, 7A, and 12. Virol. 36: 115-25, 1968.

Murakami, M., et al., An adenoviral vector expressing human adenovirus 5 and 3 fiber proteins for targeting heterogeneous cell populations. Virol. 407: 196-205, Sep. 9, 2010.

Oelmann, S., et al., Point mutations identified in Lec8 Chinese hamster ovary glycosylation mutants that inactivate both the UDP-galactose and CMP-sialic acid transporters. J. Biol. Chem. 276(28): 26291-300, Jul. 2001. (Online Apr. 2001).

Palucka, K., et al., Recent developments in cancer vaccines. J. Immunol. 186: 1325-1331, 2011.

Paul, C.P., et al., Characterization of infectivity of knob-modified adenoviral vectors in glioma. Cancer Biol. Ther. 7(5): 786-793, May 2008.

Rea, D., et al., Highly efficient transduction of human monocyte-derived dendritic cells with subgroup B fiber-modified adenovirus vectors enhances transgene-encoded antigen presentation to cytotoxic T cells. J. Immunol. 166: 5236-5244, 2001.

Renaut, L., et al. Abolition of hCAR-dependent cell tropism using fiber knobs of Atadenovirus serotypes. Virol. 321: 189-204, 2004.

Sallusto, F., et al., Dendritic cells use macropinocytosis and the mannose receptor to concentrate macromolecules in the major histocompatibility complex class II compartment: downregulation by cytokines and bacterial products. J. Exp. Med.182: 389-400, Aug. 1995.

Schwarz, F., et al., Mechanisms and principles of N-linked protein glycosylation. Curr. Opin. Struct. Biol. 21: 576-82, 2011.

Sloan, J.M., et al. MHC class I and class II presentation of tumor antigen in retrovirally and adenovirally transduced dendritic cells. Cancer Gene Ther. 9: 946-950, 2002.

Sparwasser, T., et al., Bacterial DNA and immunostimulatory CpG oligonucleotides trigger maturation and activation of murine dendritic cells. Eur. J. Immunol. 28: 2045-2054, 1998.

Stanley, P., Membrane mutants of animal cells: rapid identification of those with a primary defect in glycosylation. Mol. Cell. Biol. 5(5): 923-29, 1985.

van Raaij, M.J., et al. Structure of the human adenovirus serotype 2 fiber head domain at 1.5 A resolution. Virol. 262: 333-43, 1999.

van Raaij, M.J., et al., A triple beta-spiral in the adenovirus fibre shaft reveals a new structural motif for a fibrous protein. Nature. 401: 935-8, Oct. 28, 1999.

Verdijk, R.M., et al., Polyriboinosinic polyribocytidylic acid (poly(I:C)) induces stable maturation of functionally active human dendritic cells. J. Immunol. 163: 57-61, 1999.

van de Ven, R., et al., Selective transduction of mature DC in human skin and lymph nodes by CD80/CD86-targeted fiber-modified Adenovirus-513, J. Immunother, 32(9), 895-906, 2009.

Passinau, M., et al., Efficient Gene Transfer to Odontoblasts with Adenoviruses Displaying non-Human Knobs, IADR/AADR/CADR 85th General Session and Exhibition (Mar. 21-24, 2007), Mar. 22, 2007.

Database: Geneseq Oct. 15, 2009 "Tumour-associated antigen epitope seqid 198" retrieved from EBI accession No. GSP: ADS81113. Database accession No. ADS81113.

Database: Geneseq Apr. 28, 2011 "Control HLA-binding peptide, EBV BMLF1" retrieved from EBI accession No. GSP:ADR47126. Database accession No. ADR47126.

Database Geneseq Jun. 25, 2009 "Influenza A virus M1 epitope (residues 58-66) used as control SEQ ID: 10.", retrieved from EBI accession No. GSP:AWP80345. Database accession No. AWP80345.

Database Geneseq Jan. 22, 2009 "Human melonoma G209-2M antigen peptide, SEQ ID 4." retrieved from EBI accession No. GSP: ATM59919 Database accession No. ATM59919.

Database Geneseq Nov. 26, 2009 "Human mutant GP100 melanocyte lineage antigen peptide, SEQ ID 75.", retrieved from EBI accession No. GSP: AXQ95944 Database accession No. AXQ95944.

* cited by examiner

SEQUENCE LISTING

```
<160> NUMBER OF SEQ ID NOS: 12

<210> SEQ ID NO 1
<211> LENGTH: 9
<212> TYPE: PRT
<213> ORGANISM: Human herpesvirus 5

<400> SEQUENCE: 1

Asn Leu Val Pro Met Val Ala Thr Val
1               5

<210> SEQ ID NO 2
<211> LENGTH: 9
<212> TYPE: PRT
<213> ORGANISM: Human herpesvirus 4

<400> SEQUENCE: 2

Gly Leu Cys Thr Leu Val Ala Met Leu
1               5

<210> SEQ ID NO 3
<211> LENGTH: 9
```

```
<212> TYPE: PRT
<213> ORGANISM: Influenza A virus

<400> SEQUENCE: 3

Gly Ile Leu Gly Phe Val Phe Thr Leu
1               5

<210> SEQ ID NO 4
<211> LENGTH: 9
<212> TYPE: PRT
<213> ORGANISM: Homo sapiens

<400> SEQUENCE: 4

Ile Met Asp Gln Val Pro Phe Ser Val
1               5

<210> SEQ ID NO 5
<211> LENGTH: 9
<212> TYPE: PRT
<213> ORGANISM: Homo sapiens

<400> SEQUENCE: 5

Tyr Leu Glu Pro Gly Pro Val Thr Val
1               5

<210> SEQ ID NO 6
<211> LENGTH: 18
<212> TYPE: DNA
<213> ORGANISM: Porcine adenovirus 4

<400> SEQUENCE: 6
tgtggacggg gcctgctc                                                 18

<210> SEQ ID NO 7
<211> LENGTH: 19
<212> TYPE: DNA
<213> ORGANISM: Porcine adenovirus 4

<400> SEQUENCE: 7
tttattacag tatctgagg                                                19

<210> SEQ ID NO 8
<211> LENGTH: 20
<212> TYPE: DNA
<213> ORGANISM: Human adenovirus type 5

<400> SEQUENCE: 8
cagctccatc tcctaactgt                                               20

<210> SEQ ID NO 9
<211> LENGTH: 20
<212> TYPE: DNA
<213> ORGANISM: Human adenovirus type 5

<400> SEQUENCE: 9
ttcttgggca atgtatgaaa                                               20

<210> SEQ ID NO 10
<211> LENGTH: 18
<212> TYPE: DNA
<213> ORGANISM: Porcine adenovirus 4

<400> SEQUENCE: 10
tgtggacggg gcctgctc                                                 18
```

```
<210> SEQ ID NO 11
<211> LENGTH: 19
<212> TYPE: DNA
<213> ORGANISM: Porcine adenovirus 4

<400> SEQUENCE: 11
tttattacag tatctgagg                                              19

<210> SEQ ID NO 12
<211> LENGTH: 4
<212> TYPE: PRT
<213> ORGANISM: Mastadenovirus 4

<400> SEQUENCE: 12

Thr Leu Trp Thr
1
```

PORCINE KNOB XENOTYPE CHIMERIC ADENOVIRAL VECTOR FOR DENDRITIC CELL INFECTION

RELATED APPLICATIONS

This application claims priority to U.S. Provisional Patent Application 61/576,116 filed 15 Dec. 2011, which is incorporated by reference in its entirety.

GOVERNMENT SUPPORT

This work was made with the support of Grant 5R33AI076096-06 from the National Institutes of Health. The government of the United States of America may have certain rights in this work.

INCORPORATION-BY-REFERENCE OF SEQUENCE LISTING

The Sequence Listing, which is a part of the present disclosure, includes a computer readable form and a written sequence listing comprising nucleotide and/or amino acid sequences. The subject matter of the Sequence Listing is incorporated herein by reference in its entirety. The information recorded in computer readable form is identical to the written sequence listing.

INTRODUCTION

Dendritic cells (DCs) are an important component of innate immunity. DCs are potent antigen presenting cells (APCs) with the ability to initiate the primary immune response. Banchereau, J., et al., Annu. Rev. Immunol. 18: 767-811, 2000. In addition to their role in local innate immune responses, DCs play a crucial role in adaptive immune response by priming the immune response or by inducing tolerance. Humans have DCs with different phenotypes that are distributed throughout the body and reside at the site of potential pathogen entry or tissue injury, where they differentiate into mature DCs (Li, K., et al., Mol. Immunol. 48: 1121-1127, 2011). During maturation, DCs undergo phenotypic and functional changes allowing them to increase their antigen presenting and increase their expression of co-stimulatory molecules (Rea, D., et al., J. Immunol. 166: 5236-5244, 2001). Bacterial and viral compounds have been identified as major DC maturation signals (Sallusto, F. and Lanzavecchia, A., J. Exp. Med. 182: 389-400, 1994; Hartmann, G., et al., Proc. Natl. Acad. Sci. USA. 96: 9305-9310, 1999; Sparwasser, T., et al., J. Eur. J. Immunol. 28: 2045-2054, 1998; Verdijk, R. M., et al., J. Immunol. 163: 57-61, 1999; Cella, M., et. al., J. Exp. Med. 189: 821-829, 1999).

Since DCs have a unique ability to prime an immune response, targeting them in immune intervention strategies against infectious diseases as well as cancer has shown promise (Palucka, K., et al., J. Immunol. 186: 1325-1331, 2011). Multiple approaches have been developed to deliver antigens to DCs for presentation including transfection with DNA or RNA and gene transfer via recombinant vectors (Fong, L., et. al., Annu. Rev. Immunol. 18: 245-273, 2000; Gong, J., et al., Nat. Med. 3: 558-561, 1997). Genetic modification of DCs with recombinant viruses offers major advantages including persistent antigen presentation over time and exposure to potentially immune-activating viral components (Sloan, J. M., et al. Cancer Gene Ther. 9: 946-950, 2002). Clinical trials have shown treatment with adenovirus-based vectors are safe and with the development of transductionally targeted, selectively replicating vectors to be increasingly effective against diseases (Paul, C. P. L., et al., Cancer Biol. Ther. 7: 786-793, 2008). Paul et al. showed that replacing the fiber knob of Ad5 with certain non-human knobs enhanced infectivity of human glioma cell populations and primary tumor cells.

Infection of DCs with adenovirus is limited because human DCs lack the native adenovirus receptor, coxsackie-adenovirus receptor (CAR). Ad5 carrying subgroup B Ad fibers are more potent than classical Ad5 for gene transfer and expression in human DCs (Rea, D., et al., J. Immunol. 166: 5236-44, 2001). In order to achieve meaningful therapeutic efficacy of adenovirus-based therapies, new approaches for infection of human DCs are required.

SUMMARY

The present inventors have developed modified adenoviral vectors which can infect dendritic cells with much greater infectivity compared to wild type adenovirus. In various configurations, an adenoviral vector of the present teachings can be a chimeric adenovirus which comprises a fiber comprising a tail, a shaft and a knob, wherein the knob is a porcine knob. In some configurations, the tail can be an Ad5 tail, and the shaft can be an Ad5 shaft, so that a fiber of the present teachings can comprise an Ad5 tail, an Ad5 shaft, and a porcine knob. In some embodiments a chimeric adenovirus of the present teachings can bind dendritic cells using a receptor other than a CAR receptor. In some embodiments, a chimeric adenovirus of the present teachings can bind dendritic cells using a receptor other than an integrin receptor. In some embodiments, as chimeric adenovirus of the present teachings can bind dendritic cells using a receptor other than either a CAR receptor or an integrin receptor. In some embodiments, a chimeric adenovirus of the present teachings can comprise a fiber comprising a knob, wherein the knob comprises a galectin domain. In some configurations, a galectin domain can bind to one or more carbohydrates, such as a carbohydrate comprising lactose and N-acetyl-lactosamine units. In some configurations, a galectin domain comprised by a knob of the present teachings can bind a carbohydrate structure selected from the group consisting of Galβ1-4GlcNAcβ1-3Galβ1-4GlcNAcβ1-3Galβ1-4GlcNAc [tri(Nacetyl-lactosamine)], GlcNAcα1-4Galβ1-4GlcNAcβ1-3Galβ1-4GlcNAcβ1-3Galβ1-4GlcNAc, Galβ1-4GlcNAcβ1-3Galβ1-4Glc (lacto-N-neotetraose), Galα1-4Galβ1-4GlcNAcβ1-3Galβ1-4Glc and Galβ1-4GlcNAcβ1-3Galβ1-3GlcNAc. In some configurations, a chimeric adenovirus comprising a fiber comprising as knob of the present teachings can bind a cell-surface glycoprotein comprising a carbohydrate structure such as, without limitation, Galβ1-4GlcNAβ1-3Galβ1-4GlcNAcβ1-3Galβ1-4GlcNAc [tri(Nacetyl-lactosamine)], GlcNAcα1-4Galβ1-4GlcNAcβ1-3Galβ1-4GlcNAcβ1-3Galβ1-4GlcNAc, Galβ1-4GlcNAcβ1-3Galβ1-4Glc (lacto-N-neotetraose), Galα1-4Galβ1-4GlcNAcβ1-3Galβ1-4Glc, Galβ1-4GlcNAcβ1-3Galβ1-3GlcNAc or a combination thereof.

In various embodiments, a galectin domain comprised by a knob of the present teachings can bind to Lacto-N-neotetraose with a dissociation constant of 193±9 μM, 3-aminopropyl-lacto-N-neotetraose with a dissociation constant of 303±4 μM, 2-azidoethyl-di(N-acetyl-lactosamine) with a dissociation constant of 309±9 μM, or 2-aminoethyl-tri(N-acetyl-lactosamine) with a dissociation constant of 308±40 μM.

In various aspects, cellular uptake by a dendritic cell of DNA of a chimeric Ad5 of the present teachings can be greater than that of a wild-type Ad5. In various aspects, cellular uptake by a dendritic cell of DNA of a chimeric Ad5 of the present teachings can be as great, or greater than, that of an adenovirus comprising a knob comprising an RGD sequence. In various aspects, cellular uptake by a dendritic cell of DNA of a chimeric Ad5 can be as great, or greater than, that of an adenovirus comprising a knob comprising an adenovirus comprising a type 35 fiber.

In some embodiments, a dendritic cell of the present teachings can comprise a chimeric adenovirus-5 (Ad5) viral genome, wherein the chimeric Ad5 genome encodes a) a fiber comprising a tail, a shaft and a knob, wherein the knob is a porcine knob; and b) a promoter operably linked to a heterologous sequence encoding an antigen peptide.

In some embodiments, the present teachings include ex vivo cell cultures comprising a dendritic cell, in particular a human dendritic cell, wherein the dendritic cell comprises nucleic acid sequences encoding Ad5 sequences encoding a modified tail that includes a porcine knob sequence, as described herein.

In some embodiments, the present teachings include a vaccine comprising an Ad5 modified to comprise a porcine knob, as well as an antigen peptide sequence such as, for example, an antigen peptide consisting of a linear peptide of from at least 8 up to 15 amino acids, for example 9 amino acids such as a peptide sequence set forth in table 1.

In some embodiments, a vaccine of the present teachings can comprise a dendritic cell comprising Ad5 sequences encoding a modified tail protein, such as a tail protein comprising a porcine knob. In some configurations, a vaccine can comprise dendritic cells autologous to a subject such as a human subject, in which dendritic cells obtained from the subject can be grown and/or infected with a modified Ad5 of the present teachings in a cell culture ex vivo. Such cells can be administered to a subject, such as, for example, the donor of the dendritic cells, using methods well known to skilled artisans.

In some embodiments of the present teachings, a subject such as a human can receive a vaccination through administration of a modified Ad5 of the present teachings. In some embodiments, a subject such as a human can receive a vaccination through administration of dendritic cells infected with an Ad5 of the present teachings. In some configurations, the dendritic cells can be autologous dendritic cells.

In various configurations, an antigen peptide sequence can comprise or consist of from about 8, at least 8 up to 15, or about 15, contiguous amino acids. In some configurations, an antigen peptide sequence can comprise or consist of 9 contiguous amino acids. In various aspects, a peptide sequence can be that of a protein fragment, wherein the protein is a pathogen protein or a cellular protein, such as, for example, a protein expressed by a cancer cell. In some aspects, an antigen can comprise an antigen peptide such as that of an HLA-A restricted peptide or HLA-B restricted peptide. In some aspects, an antigen peptide can comprise or consist of a sequence as set forth in Table 1.

TABLE 1

Antigen Peptide Sequences

| Name | Source | Sequence | Identification |
|---|---|---|---|
| CMVpp65 | Cytomegalo-virus | NLVPMVATV | SEQ ID NO: 1 |
| EBV BMLF 1 | Ebstein-Barr virus | GLCTLVAML | SEQ ID NO: 2 |
| fluM1 | Influenza A virus | GILGFVFTL | SEQ ID NO: 3 |
| G209-2M | human melanoma | IMDQVPFSV | SEQ ID NO: 4 |
| G280-9V | human melanoma | YLEPGPVTV | SEQ ID NO: 5 |

Various embodiments of the present teachings include a dendritic cell comprising a chimeric adenovirus-5 (Ad5) viral genome, wherein said chimeric Ad5 genome encodes a) a fiber comprising a tail, a shaft and a knob, wherein the knob is a porcine knob; and b) a promoter operably linked to a heterologous sequence encoding an immunizing antigen. As used herein, an "immunizing antigen" is a protein, polypeptide or oligopeptide that can stimulate an immune response in a body such as a human body.

In some embodiments, the present teachings include an ex vivo cell culture comprising a dendritic cell comprising a chimeric Ad5 genome which encodes a) a fiber comprising a tail, a shaft and a knob, wherein the knob is a porcine knob; and b) a promoter operably linked to a heterologous sequence encoding an immunizing antigen. For example, an antigen that can bind a corresponding MHC class I heavy chain or MHC class I-like antigen presenting molecule such as CD1 (Altamirano, M. M., et al., Proc. Nat'l Acad. Sci. 98: 3288-3293, 2001). In some aspects, an immunizing antigen can be that of a peptide which can be presented by an MHC class I molecule.

In some embodiments, the present teachings include vaccines, wherein a vaccine comprises a dendritic cell comprising a chimeric Ad5 genome which encodes a) a fiber comprising a tail, a shaft and a knob, wherein the knob is as porcine knob; and b) a promoter operably linked to a heterologous sequence encoding an immunizing antigen. In various configurations, an immunizing antigen can be a peptide comprising or consisting of about 8, from 8 to 15, or about 15 contiguous amino acids. In various configurations, an immunizing antigen can be a peptide comprising or consisting of 9 contiguous amino acids, or about 9 contiguous amino acids. In various configurations, an immunizing antigen can be a peptide comprising or consisting of a sequence selected from the group consisting of NLVPMVATV (SEQ ID NO: 1), GLCTLVAML (SEQ ID NO: 2), GTLGFVFTL (SEQ ID NO: 3), IMDQVPFSV (SEQ ID NO: 4) and VLEPGPVTV (SEQ ID NO: 5).

Various embodiments of the present teachings include a chimeric Ad5 comprising: a) a fiber comprising a tail, a shaft and a knob, wherein the knob is a porcine knob; and b) a promoter operably linked to a heterologous sequence encoding an immunizing antigen. In various configurations, an immunizing antigen can comprise or consist of a sequence of a protein expressed by a cell at a level associated with a disease. In various configurations, an immunizing antigen can comprise or consist of a sequence of a protein expressed by a cancer cell at a level associated with a cancerous phenotype. In various configurations, an immunizing antigen can comprise or consist of about 8, from 8 to 15, or about 15 contiguous amino acids. In various configurations, an immunizing antigen can comprise or consist of 9, or about 9 contiguous amino acids. In various configurations, an immunizing antigen can comprise or consist of a peptide having a sequence selected from the group consisting of NLVPM- VATV (SEQ ID NO: 1), GLCTLVAML (SEQ ID NO: 2), GILGFVFTL (SEQ ID NO: 3), IMDQVPFSV (SEQ ID NO: 4) and YLEPGPVTV (SEQ ID NO: 5).

DETAILED DESCRIPTION

Figure 1:
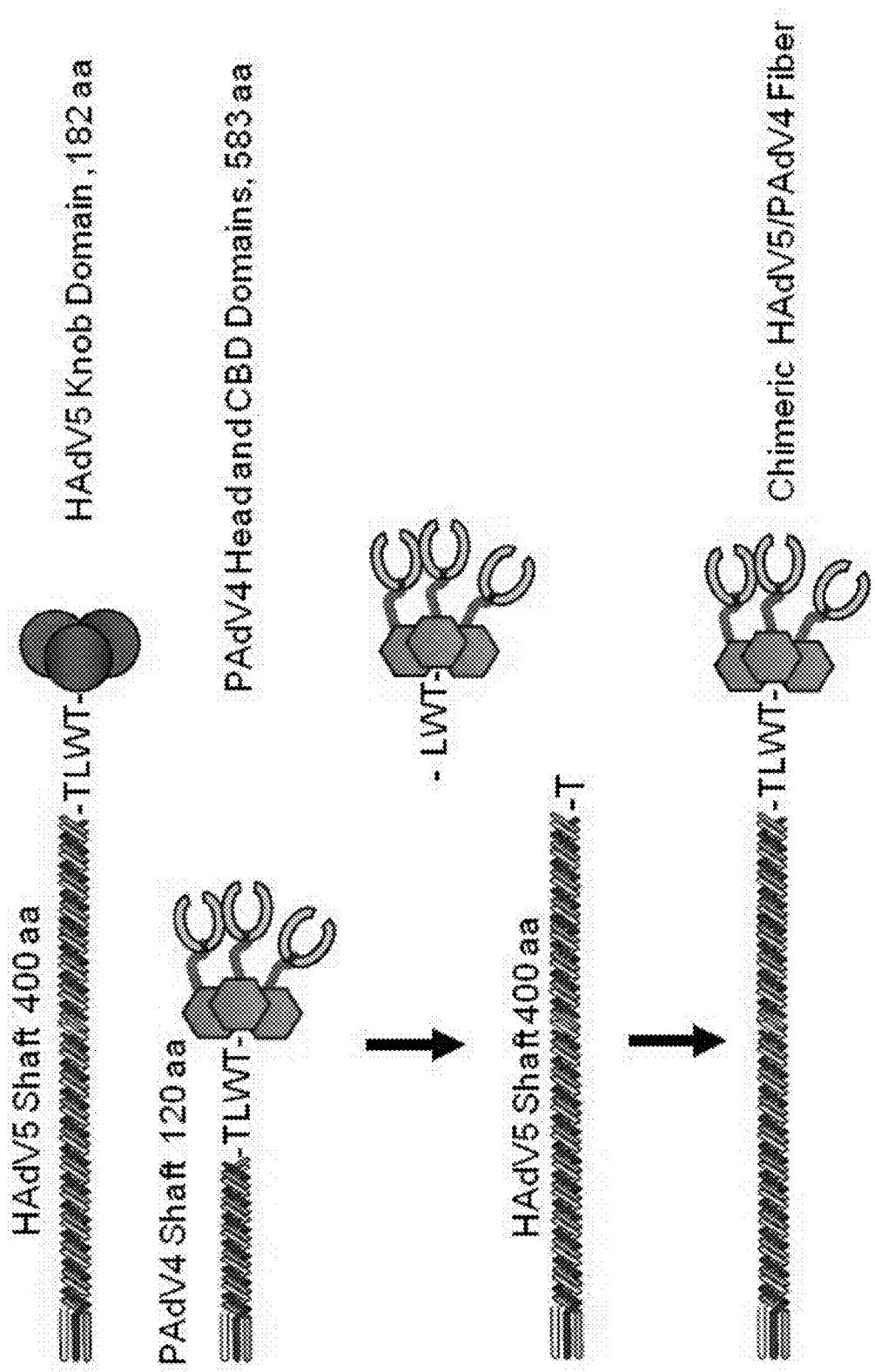
FIG. 1 illustrates the design of the Ad5Luc1-PK chimeric fiber.

The present inventors disclose a chimeric adenovirus and methods of transforming dendritic cells therewith. These methods, in various configurations, can enhance infectivity adenovirus towards human dendritic cells. In various embodiments, a porcine knob, which contains a galectin domain, is able to bind to carbohydrate moieties on the cell surface of dendritic cells. In some configurations, the carbohydrate moieties can comprise lactose and N-acetyl-lactosamine units. Furthermore, in some configurations the lactose and N-acetyl-lactosamine units can be Galβ1-4GlcNAcβ1-3Galβ1-4GlcNAcβ1-3Galβ1-4GlcNAc [tri(Nacetyl-lactosamine)], GlcNAcα1-4Galβ1-4GlcNAcβ1-3Galβ1-4GlcNAcβ1-3Galβ1-4GlcNAc, Galβ1-4GlcNAcβ1-3Galβ1-4Glc (lacto-N-neotetraose), Galα1-4Galβ1-4GlcNAcβ1-3Galβ1-4Glc, Galβ1-4GlcNAcβ1-3Galβ1-3GlcNAc or a combination thereof. In various configurations the galectin domain can bind to Lacto-N-neotetraose with a dissociation constant of 193+9 μM, to 3-aminopropyl-lacto-N-neotetraose with a dissociation constant of 303±4 μM, to 2-azidoethyl-di(N-acetyl-lactosamine) with a dissociation constant of 309±9 μM, or to 2-aminoethyl-tri(N-acetyl-lactosamine) with a dissociation constant of 308±40 μM (the SPR response in μRIU).

Monocytes and dendritic cells (DCs), such as freshly isolated human blood myeloid DCs, plasmacytoid DCs and monocyte-derived DCs lack CAR expression, but Langerhans cells and dermal DCs from skin express CAR. Furthermore, monocyte-derived DCs have lower CD46 expression then dermal DCs, Langerhans DCs, myeloid DCs, and plasmacytoid DCs. Expression of CAR and CD46 (the subgroup C and B adenovirus receptors) on dendritic cell surfaces can be measured using FACS in cell lines. The correlation between infectivity enhancement and expression levels of CAR and CD46 can be determined.

For example, infectivity of a panel of fiber-modified Ads that are CAR-independent can be compared in a variety of cancer cell types. The fiber-modified Ads can be examined to determine gene transfer to dendritic cell lines and compared with a tropism-modified Ad vector, Ad5/3, which encodes a fiber composed of the native Ad5 tail and shaft domains, but the fiber knob domain from Ad3.

In some configurations, Ad5Luc1-PK and Ad5Luc1-CK1 fiber-modified adenovirus vectors of the present teachings can be Ad vectors with enhanced infectivity toward dendritic cells in comparison to an Ad5 comprising a wild-type knob. For example, three of the fiber-modified vectors, Ad5Luc1-PK, Ad5Luc1-CK1 and Ad5/3, can exhibit enhanced infectivity towards human dendritic cells compared to Ad5Luc1. In some configurations, Ad5Luc1-PK and Ad5Luc1-CK1 can have more than a 10-fold greater infectivity compared to that of Ad5/3. In some configurations, an Ad5Luc1-PK can have a greater infectivity compared to that of an Ad5 with a type 35 fiber described in Rea et al. (J. Immunol. 166: 5236-44, 2001).

Methods

Methods and compositions described herein utilize laboratory techniques well known to skilled artisans. Such techniques can be found in laboratory manuals such as Sambrook, J., et al., Molecular Cloning: A Laboratory Manual, 3rd ed. Cold Spring Harbor Laboratory Press, Cold Spring Harbor, N.Y., 2001; Spector, D. L. et al., Cells: A Laboratory Manual, Cold Spring Harbor Laboratory Press, Cold Spring Harbor, N.Y., 1998; Harlow, E., Using Antibodies: A Laboratory Manual, Cold Spring Harbor Laboratory Press, Cold Spring Harbor, N.Y., 1999.

The following materials and methods are used in some experiments reported herein.

Plasmid construction. A 1,750-bp region containing the PAdV-4 fiber knob and carbohydrate binding domains (amino acids 121-703) of the fiber protein was amplified from cell lysates containing wild type PAdV-4 virus obtained from the US Department of Agriculture National Veterinary Services Laboratory (Ames, Iowa) using the following primers: (PAd4 knob fwd) 5'-TGTGGACGGGGCCTGCTC-3' (SEQ ID: 6) and (PAd4 knob rev) 5'-TTTATTACAGTATCTGAGG-3' (SEQ ID: 7). Plasmid pSHAFT, a cloning vector containing the Ad5 fiber gene with the knob region deleted and replaced by a small linker containing SmaI and EcoICR1 restriction sites (Krasnykh, V. N., et al., J. Virol. 70: 6839-46, 1996), was linearized by SmaI and EcoICR1 digestion, leaving two blunt ends. Following gel purification, the PAdV-4 knob domain PCR product was ligated into linearized pSHAFT resulting in pSHAFT-PK and positive clones were screened for correct orientation via restriction enzyme digest. This plasmid contains the chimeric fiber gene encoding the complete Ad5 fiber shaft in-frame with the PAdV-4 knob domain. A stop codon and poly-adenylation sequence is present at the 3' end. The chimeric fiber gene in pSHAFT was digested with NcoI and MunI to liberate the DNA fragment containing the carboxy terminus of the HAdV-5 shaft and the PAdV-4 knob domain. This fragment was ligated into the NcoI-MunI-digested fiber shuttle vector pNEB.PK.3.6 (Krasnykh, V. N., et al., J. Virol. 70: 6839-46, 1996), resulting in pNEB.PK.3.6-PK.

Generation of recombinant adenovirus. The recombinant Ad5Luc1-PK genome containing the chimeric PAdV-4 fiber gene was derived by homologous recombination in *E. coli* BJ5183 with SwaI-linearized rescue plasmid pVK700 (Belousova, N., et al., J. Virol. 76: 8621-31, 2002) and the fiber-containing PacI-KpnI-fragment of pNEB.PK.3.6-PK, essentially as described (Krasnykh, V., et al., J. Virol. 72: 1844-52, 1998). Plasmid pVK700 is derived from pTG3602 (Chartier, C., et al., J. Virol. 70: 4805-10, 1996), but contains an almost complete deletion of the fiber gene and contains a firefly luciferase reporter gene driven by the cytomegalovirus immediate early promoter in place of the E1 region. The recombinant genome of Ad5GFP1-PK containing the chimeric PAdV-4 fiber gene was derived by homologous recombination in *E. coli* BJ5183 with fiber shuttle plasmid pKan3.1-PK which contains the same chimeric fiber gene as pNEB.PK.3.6-PK described above, and SwaI-linearized rescue plasmid pVK900 (Murakami, M., et al., Virol. 407: 196-205, 2010). Plasmid pVK900 is a fiber-deleted HAdV-5 genome plasmid essentially the same as pVK700 except that EGFP is encoded in the E1 region (supplied by Victor Krasnykh, University of Texas MD Anderson Cancer Center). All genomic clones were sequenced and analyzed by PCR prior to transfection of HEK 293 cells. Ad5Luc1 is a replication defective E1-deleted Ad vector containing a firefly luciferase reporter gene driven by a cytomegalovirus promoter (Krasnykh, V., et al., J. Virol. 75: 4176-83, 2001). All vectors were propagated on HEK 293 cells and purified by equilibrium centrifugation in CsCl gradients by standard protocols. Viral particle concentration was determined at 260 nm by the method of Maizel et al. (Maizel, J. V., et al., Virol. 36: 115-25, 1968) by using a conversion factor of $1.1 \times 10^{12}$ viral particles/absorbance unit.

Generation of Monocyte-Derived DC.

DC medium is RPMI+2 mM glutamine+HEPES+non-essential amino-acids+Pen/Strep+1% AB sera.

Peptide pulsing medium is Stemline+2 mM L-glutamine+Pen/Strep+1% AB sera A-DC generation.

1) Fresh PBMC are isolated from blood, buffy coats or leukopheresis as instructed on protocol. Frozen PBMC (yield $\sim 2 \times 10^8$ cells/vial) are thawed, counted. Fresh or frozen PBMC are adjusted to $5 \times 10^6$/ml in DC media. Transfer 40 ml ($2 \times 10^8$ cells) to a T175 flask and incubate for 2 h at 37° C.

2) Remove non-adherent cells and transfer to a 50 ml conical tube. Wash T175 gently 2× with 25 ml PBS and transfer to another 50 ml conical tube.
   a. These PBL can be discarded or can be used as a source of T cells (see Primary CTL stimulation protocol).

3) To T175 ml flask add 30 ml DC media containing 100 ng/ml GM-CSF (Leukine) and 20 ng/ml IL-4 (CellGenix). Incubate cells at 37° C. 5% CO2.

4) On day 3 feed cells with 10 ml DC medium containing 100 ng/ml GM-CSF and 20 ng/ml IL-4.

5) Harvest cells on day 6 by gently rocking flask back and forward; collect non-adherent and loosely adherent cells and transfer to a 50 ml conical tube. Wash T175 flask gently 2× with 25 ml PBS and transfer to another 50 ml conical tube. Spin at 1500 RPM for 5 min, aspirate supernatant, resuspend cells in DC medium (1-2 ml/tube), pool cells and count. DC are adjusted to $2 \times 10^6$/ml in DC media containing 200 ng/ml GM-CSF and 40 ng/ml IL-4 (2× concentration)

Yield: frozen PBMC $\sim 2$-$5 \times 10^6$ DC/flask; from fresh cells $\sim 10^7$ DC/flask.

B-CD40L/IFN-γ maturation

6) Immature DC consist of cells grown in GM-CSF and IL-4; diluted 1:1 vol with DC media.

7) J558-muCD40L or K562-huCD40L are used for maturation. Cells are irradiated (5,000 RADS for J558 or 10,000 RADS for K562), spun and resuspend in DC media at a $4 \times 10^5$ cells/ml in DC media.

8) Mix 1:1 vol of DC to CD40L-expressing cells, up to 4 ml per well of a 6 well tray (Ultra-low #3471). Ratio of DC to CD40L cells is 5DC:1CD40L-expressing cell.

9) Add 100 u/ml IFN-g (Actimmune). Incubate for 24-48 h

10) Harvest DC, save undiluted supernatant for assessment of cytokine production. Wash cells once, and resuspend in Peptide pulsing media if cells are to be use in stimulation of T cells.

NOTE: Immature (GM-CSG/IL-4) and mature (GM-CSG/IL-4+CD40L+IFN-γ) are characterized by production of IL-12p70 (ELISA) and up-regulation of HLA-DR. CD86 and CD83 (all markers vs. CD11c, by FACS).

PCR Analysis of the Fiber Region. Genomic DNA contained in Ad5Luc1, Ad5Luc1-PK and PAdV-4 viral particles was used as templates for PCR amplification of fiber genes using a HAdV-5-specific primer set: (fwd) 5'-CAGCTC-CATCTCCTAACTGT-3' (SEQ ID: 8) and (rev) 5'-TTCT-TGGGCAATGTATGAAA-3' (SEQ ID: 9) and a PAdV-4-specific primer set: (fwd) 5'-TGTGGACGGGGCCTGCTC-3' (SEQ ID: 10) and (rev) 5'-TTTATTACAGTATCTGAGG-3' (SEQ ID: 11). Wild type PAdV-4 virus was used as a positive control.

Western Blot Analysis. Purified Ad virions ($5.0 \times 10^9$) were diluted in Laemmli buffer and incubated at room temperature (unboiled samples) or 95° C. (boiled samples) for 10 minutes and loaded onto a 4-20% gradient SDS-polyacrylamide gel (Bio-Rad, Hercules, Calif.). Following electrophoretic separation, Ad capsid proteins were electroblotted onto a PVDF membrane and detected with a 4D2 monoclonal anti-fiber tail primary antibody diluted 1/3000 (Lab Vision, Freemont Calif.). Immunoblots were developed by addition of a secondary horseradish peroxidase-conjugated anti-mouse immunoglobulin antibody at a 1/3000 dilution (Dako Corporation, Carpentaria, Calif.), followed by incubation with 3-3'-diaminobenzene peroxidase substrate, DAB, (Sigma Chemical Company, St. Louis, Mo.).

Ad-Mediated Gene Transfer Assays. Cells were plated in 24-well plates and were transduced for 1 hour at 37° C. with each Ad vector diluted to 100-300 viral particles/cell in 500 μL of transduction media containing 2% FBS. Following the incubation, virus-containing media was replaced with fresh media containing 2% FBS and cells were maintained at 37° C. in an atmosphere containing 5% $CO_2$. Cells were harvested 24 hours post-transduction in passive lysis buffer and gene transfer was determined using a luciferase activity assay system (Promega, Madison, Wis.). Fluorescence microscopy was performed with an inverted IX-70 microscope (Olympus) using a 20× objective. Cells were infected with Ad5GFP1-PK for 24 hours prior to imaging.

For experiments assessing the competitive inhibition containing of vector binding to cells, recombinant fiber knob protein (Glasgow, J. N., et al., Virol. 324: 103-16, 2004) at 0.5, 5.0 and 50 μg/ml final concentration or recombinant PAdV-4 carbohydrate binding domain (CBD) protein [20] at 0.5, 5.0, 50 and 100 μg/ml was incubated with various cell lines at 37° C. in media containing 2% FBS for 20 minutes prior to the addition of HAdV-5 vectors. Following transduction with Ad vectors, cells were rinsed with media to remove unbound virus and blocking proteins, and were maintained at 37° C. in an atmosphere containing 5% $CO_2$.

To inhibit glycosylation of cellular proteins, chemical inhibitors of glycosylation were used. CHO-Pro5 cells were incubated with medium containing 10 μg/ml swainsonine (Sigma, Saint Louis, Mo., S8195) and/or 1 μg/ml benzyl-α-GalNAc (Sigma B4894) for 24 hr at 37° C., followed by addition of Ad vectors in media containing 2% FBS.

EXAMPLES

The present teachings including descriptions provided in the Examples that are not intended to limit the scope of any claim or aspect. Unless specifically presented in the past tense, an example can be a prophetic or an actual example. The following non-limiting examples are provided to further illustrate the present teachings. Those of skill in the art should, in light of the present disclosure, appreciate that many changes can be made in the specific embodiments that are disclosed and still obtain a like or similar result without departing from the spirit and scope of the present teachings.

Example 1

This example illustrates the generation of a fiber-modified HAdV-5 vector containing the PAdV-4 knob and carbohydrate binding domains.

The fiber protein of PAdV-4 NADC-1 is comprised of a homotrimer of 703 amino acids (FIG. 1). Predicted functional domains include a tail domain (residues 1-37) containing penton interaction sequence, a short shaft domain (residues 38-120) with six predicted triple beta-spiral repeats (van Raaij, M. J., et al. Virol. 262: 333-43, 1999) and a fiber knob domain homologous to other Ad fiber knob domains (residues 121-287) (Guardado-Calvo, P., et al. Acta. Crystallogr. Sect. F Struct. Biol. Cryst. Commun. 65: 1149-52, 2009). This fiber also contains a unique C-terminal domain composed of two tandem carbohydrate binding domains (CBDs) (residues 393-681) that bind carbohydrates containing lactose and N-acetyl-lactosamine units (Guardado-Calvo, P., et al. J. Virol. 84: 10558-68, 2010). Almost all mastadenoviruses contain a conserved threonine-leucine-tryptophan-threonine (TLWT) (SEQ ID NO: 12) motif at the N-terminus of the fiber knob domain, and in human Ad2 and Ad5 a flexible region separating the shaft and the knob domains precedes this motif (van Raaij, M. J., et al. Nature. 401: 935-8, 1999). The modular fiber structure was used to substitute the coding region of the PAdV-4 knob and CBD domains for the HAdV-5 fiber knob sequence while retaining the TLWT motif common to both fibers (Renaut, L., et al. Virol. 321: 189-204, 2004). A recombinant E1-deleted HAdV-5 genome (Ad5Luc1-PK) containing the chimeric HAdV-5 shaft/PAdV-4 fiber gene and a firefly luciferase reporter gene controlled by the CMV immediate early promoter/enhancer were constructed. The Ad5Luc1-PK vector was rescued following transfection of HEK 293 cells and large-scale preparations of Ad5Luc1-PK and the Ad5Luc1 control vector were produced and purified by double CsCl gradient centrifugation. Ad5Luc1-PK viral particle concentration in full preparations ranged from $1.2 \times 10^{11}$ to $1.25 \times 10^{12}$ viral particles/ml, similar to that of the Ad5Luc1 control vector containing the HAdV-5 wild type fiber. The Ad5Luc1 vector is isogenic to Ad5Luc1-PK except for the fiber protein.

The fiber genotypes of Ad5Luc1 and Ad5Luc1-PK vectors were confirmed via diagnostic PCR using primer pairs specific for the fiber knob domain and genomes from purified virions as PCR templates. Genomic DNA from wild type PAdV-4 was used as a positive control. The expected PCR products were observed for the wild type HAdV-5 fiber knob domain (530 bp) and the PAdV-4 fiber knob and CBD domains (1,750 bp) (FIG. 2A).

Figure 2:
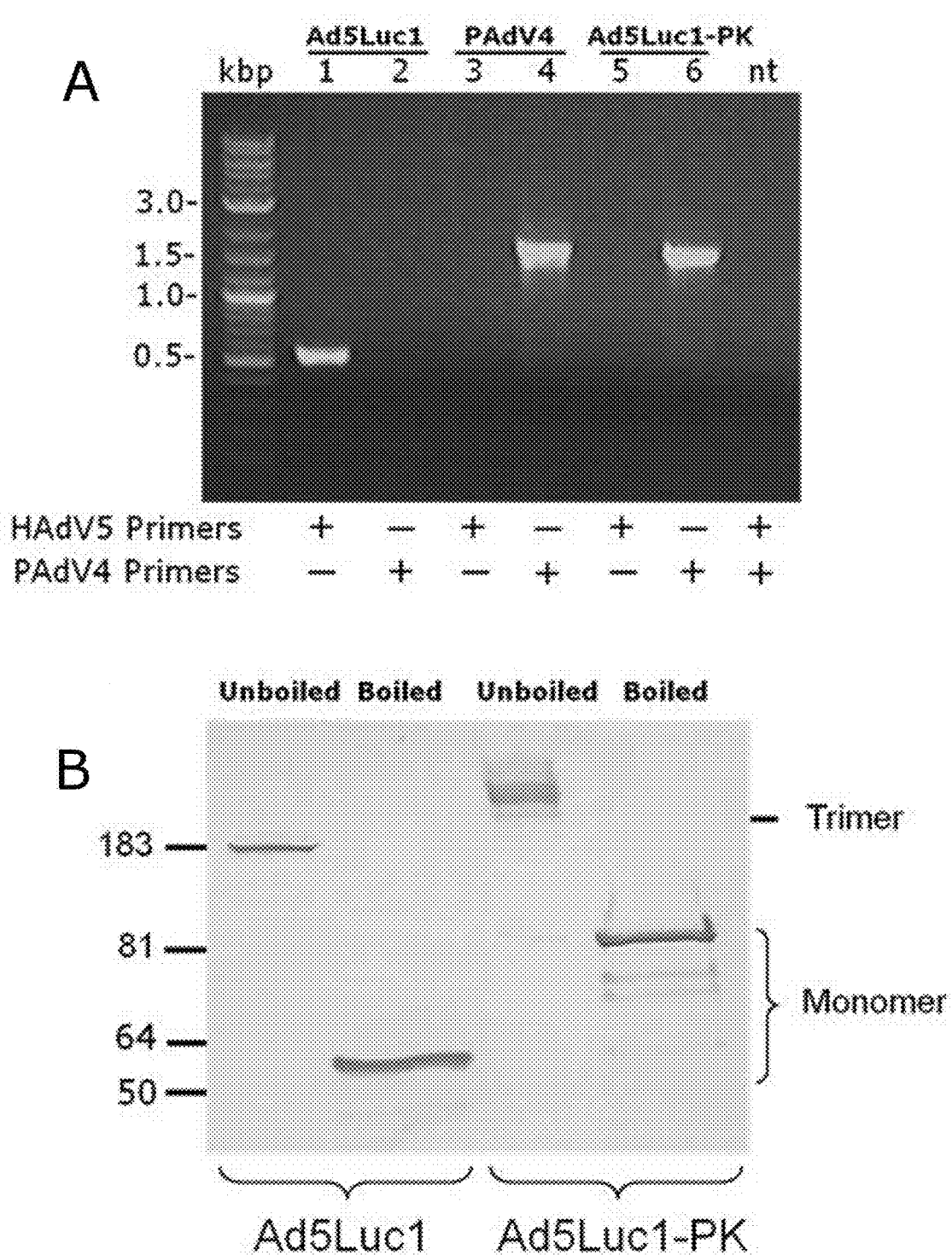
FIG. 2 illustrates molecular validation of Ad5Luc1-PK virions.

SDS-PAGE was performed followed by western blot analysis on purified viral particles to verify that Ad5Luc1-PK virions contain correctly trimerized chimeric fiber proteins (FIG. 2B). Blots were probed with a monoclonal primary antibody (4D2) directed against the fiber tail domain common to both HAdV-5 and chimeric fiber molecules. In samples that were not heat denatured (FIG. 2B, unboiled) bands were observed at 183 kDa and an estimated 250 kDa, corresponding to trimers of the HAdV-5 fiber and chimeric fibers, respectively. Further, bands in boiled samples resolved at apparent molecular masses of 60 kDa for the wild type HAdV-5 fiber and 90 kDa for the chimeric fiber in Ad5Luc1-PK, representing fiber monomers.

Example 2

This example illustrates that Ad5-PK vector infectivity is independent of CAR.

Figure 3:
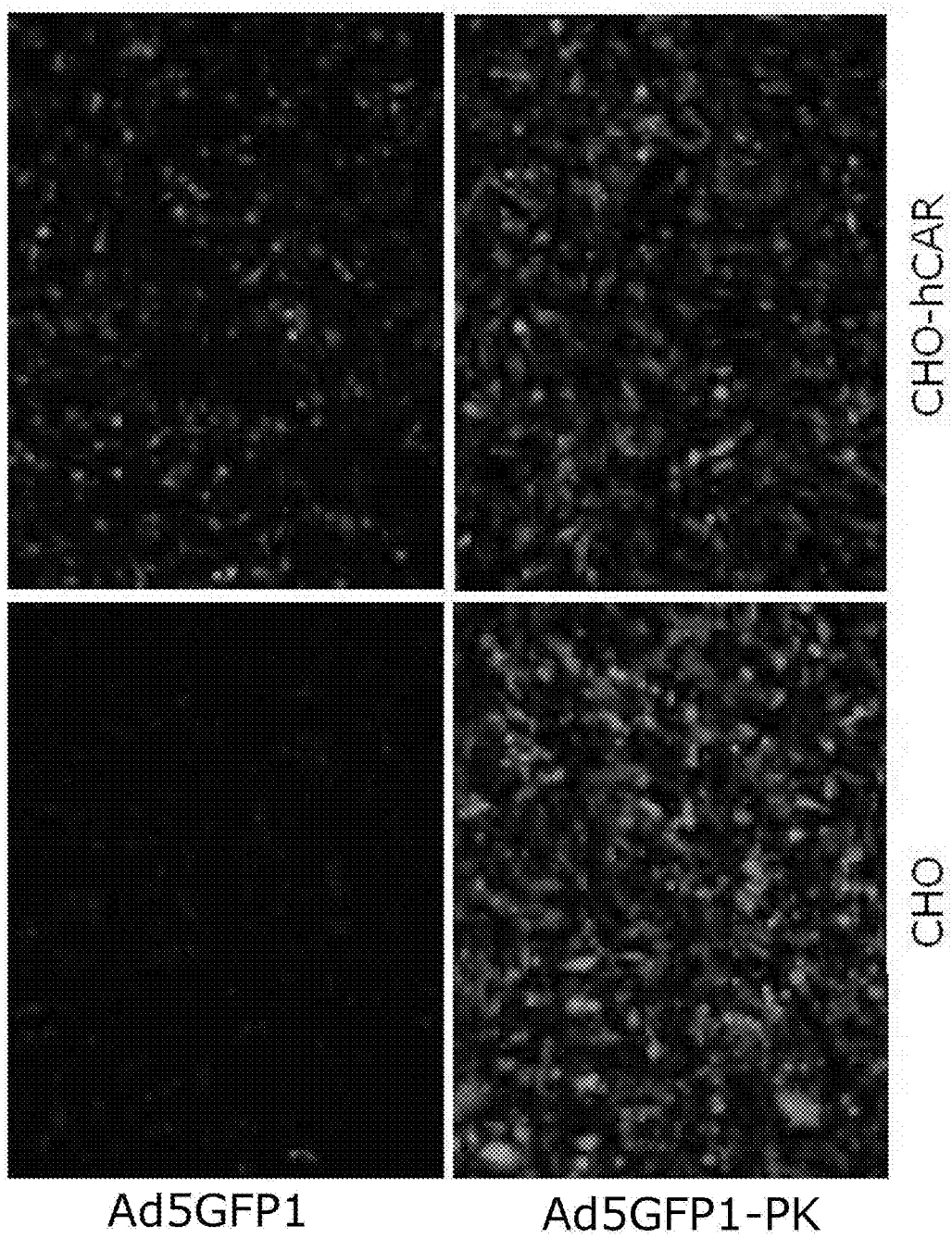
FIG. 3 illustrates fluorescence micrographs of CAR-negative CHO and CAR-positive CHO-hCAR cell lines.
Figure 4:
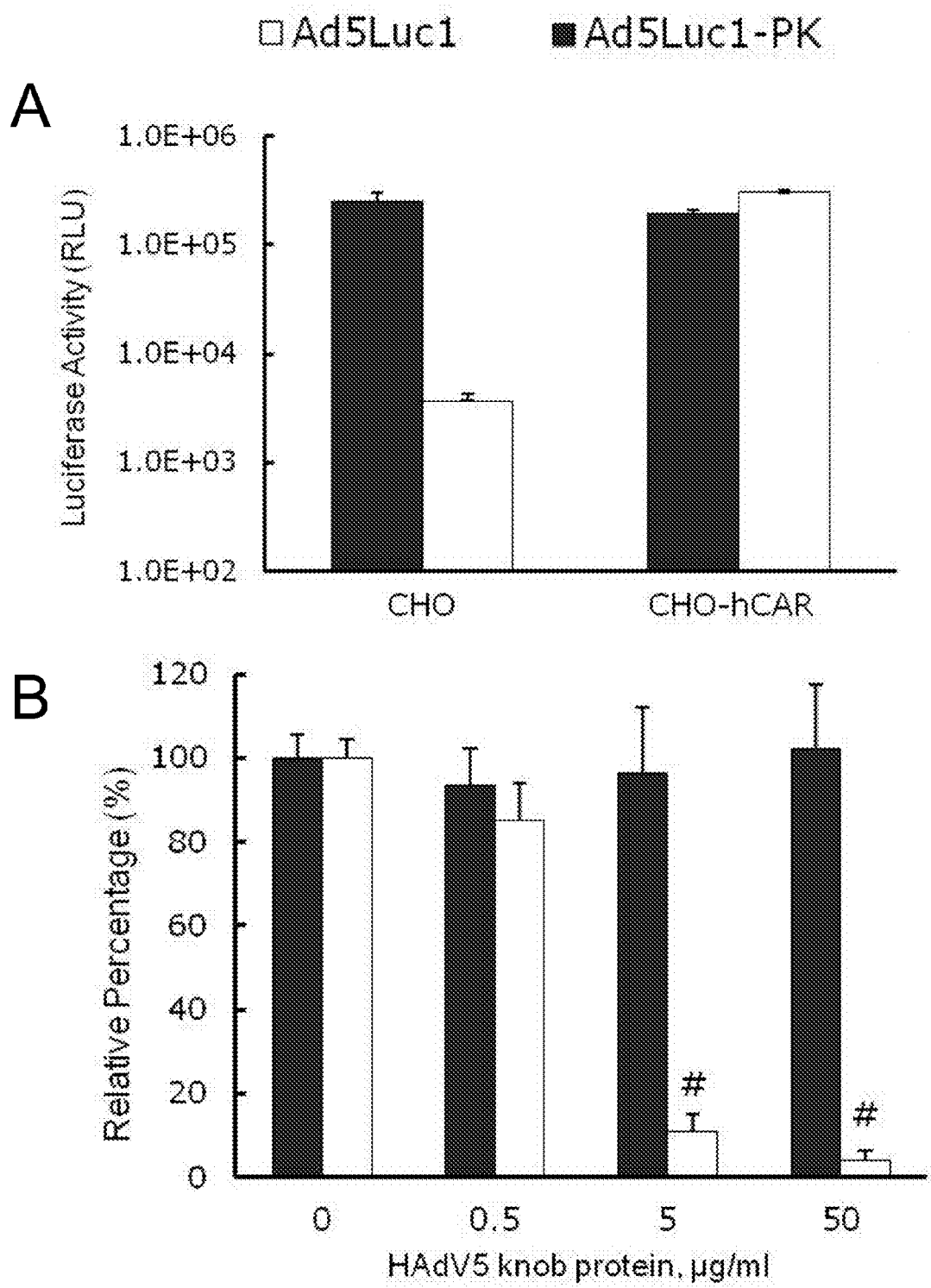
FIG. 4 illustrates that gene transfer of Ads-PK vectors is CAR-independent.

High resolution crystal structure analysis has shown that the A-B loop in the N-terminal region of the PAdV-4 knob domain is structurally similar to the A-B loop in the CAR-binding domain in adenoviruses that use CAR as a primary receptor, but that only one CAR-binding residue is conserved (Guardado-Calvo, P., et al. J. Virol. 84: 10558-68, 2010). To investigate whether Ad5-PK vectors exhibit CAR-dependent tropism, gene transfer assays were performed in two cell lines with markedly different levels of CAR expression: CAR-deficient Chinese hamster ovary (CHO) cells and a CHO-derived cell line, CHO-hCAR, which stably expresses human CAR (Bergelson, J. M., et al. Science. 275: 1320-3, 1997). CHO and CHO-hCAR cells were infected with the Ad5GFP control vector and Ad5GFP1-PK, a vector isogenic to Ad5Luc1-PK except that the firefly luciferase reporter gene was replaced with green fluorescent protein, GFP. Fluorescence microscopy showed GFP expression in CHO-hCAR cells but not in CAR-deficient CHO cells (FIG. 3), consistent with native HAdV-5 tropism. In contrast, Ad5Luc1-PK-mediated GFP gene delivery does not depend on CAR expression, as similar number of GFP-positive cells were observed in both the CHO and CHO-hCAR cell lines. Similar gene transfer assays were performed using luciferase-expressing Ad5Luc1 and Ad5Luc1-PK vectors to quantify differences in gene delivery based solely on CAR expression. Ad5Luc1 exhibited the expected CAR-dependent tropism as demonstrated by an 80-fold increase in luciferase activity in CHO-hCAR cells versus CHO cells (FIG. 4A). In contrast, Ad5Luc1-PK provided robust gene delivery to both cell lines. In addition, competitive inhibition of CAR binding with recombinant HAdV-5 knob proteins (50 μg/ml) inhibited over 96% of Ad5Luc1 gene transfer to CHO-hCAR cells, but did not inhibit the gene transfer of Ad5Luc1-PK (FIG. 4B).

Example 3

This example illustrates that Ad5Luc1-PK uses carbohydrate binding domains for gene transfer.

Figure 5:
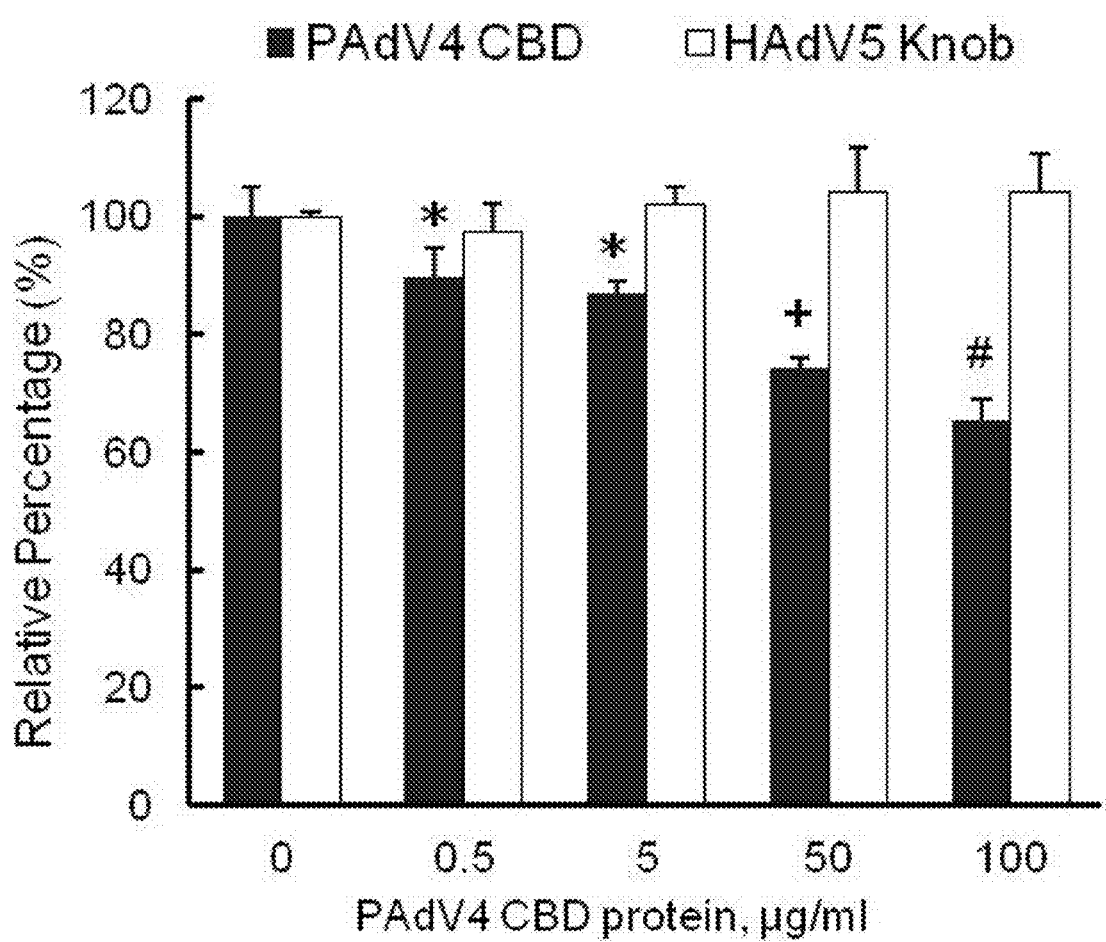
FIG. 5 illustrates that Ad5Luc1-PK uses carbohydrate binding domains for gene transfer.

To determine whether the CBDs in the chimeric fiber of Ad5Luc1-PK participate in cellular attachment, competitive inhibition assays were performed using a recombinant protein consisting of the tandem PAdV-4 CBDs (residues 393-703 of the PAdV-4 fiber protein) or recombinant HAdV-5 fiber knob protein as a negative control. Addition of PAdV-4 CBD protein during infection caused a dose-dependent inhibition of Ad5Luc1-PK-mediated gene transfer with a maximum inhibition of 35% at 100 μg/ml (FIG. 5), indicating that the CBDs in the chimeric fiber are responsible for cellular attachment during infection.

Figure 6:
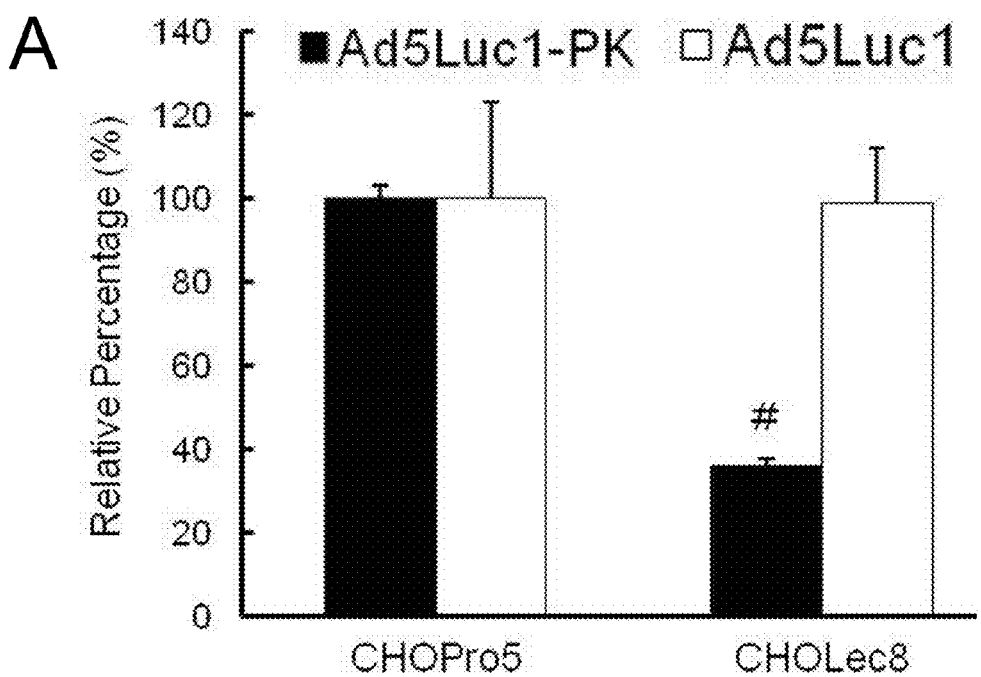
FIG. 6 illustrates that Ad5Luc1-PK-mediated gene delivery is mediated by glycans containing lactose.
Figure 6:
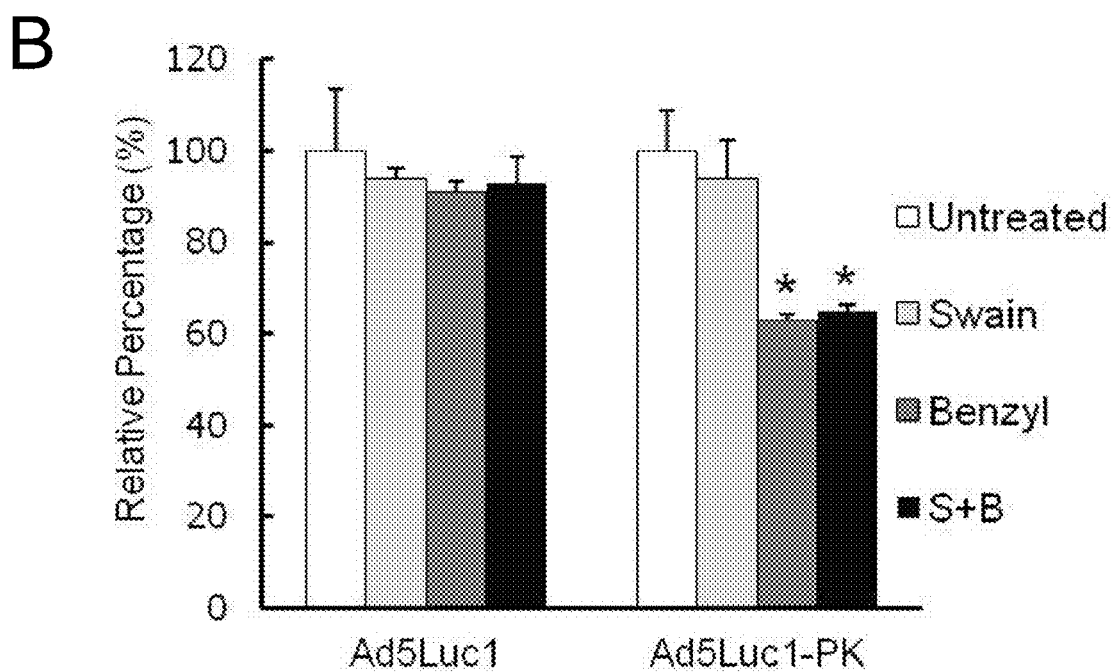

The CBDs within the PAdV-4 fiber protein bind to lactose, N-actyl-lactosamine and poly-N-acetyl-lactosamine in order of increasing affinity (Guardado-Calvo, P., et al., J. Virol. 84: 10558-68, 2010). However, whether the CBDs in the PAdV-4 chimeric fiber recognize these glycans and use them as a means for viral transduction is not known. Gene transfer assays were performed in the CHO-Lec8 cells which contains mutations in the UDP-galactose transporter/translocase (UGT) gene (Deutscher, S. L., et al., J. Biol. Chem. 261:

96-100, 1986; Stanley, P., Mol. Cell. Biol. 5: 923-29, 1985; Oelmann, S., et al., J. Biol. Chem. 276: 26291-300, 2001), and lack the ability to galactosylate glycoproteins and therefore produce glycoproteins with truncated carbohydrate chains that lack lactose, N-acetyl-lactosamine and poly-N-acetyl-lactosamine. The level of Ad5Luc1 gene delivery was unchanged between CHO-Lec8 cells and the control CHO-Pro5 cells that exhibits normal glycosylation (FIG. 6A). In contrast, Ad5Luc1-PK gene delivery to CHO-Lec8 cells was reduced by 64% compared to the control CHO-Pro5 cells, showing that the presence of lactose-containing glycans at the cell surface is critical for Ad5Luc1-PK infectivity.

There are two major types of carbohydrate chains on glycoproteins: N-linked glycans linked to asparagine residues and O-linked glycans linked to serine or threonine (Li, H., and d'Anjou, M., Curr. Opin. Biotechnol. 20: 678-84, 2009; Schwarz, F., and Aebi, M., Curr. Opin. Struct. Biol. 21: 576-82, 2011; Dwek, R. A., Chem. Rev. 96: 683-720, 1996). To further investigate the nature of the glycans recognized during Ad5Luc1-PK infection, gene transfer assays were performed following incubation of CHO-Pro5 cells with inhibitors of N-linked glycan synthesis (swainsonine, 10 µg/ml), or O-linked glycan synthesis (benzyl-α-GalNAc, 1 µg/ml) (Elbein, A. D., et al., Proc. Natl. Acad. Sci. USA. 78: 7393-7, 1989; Kuan, S. F., et al., J. Biol. Chem. 264: 19271-7, 1989). The addition of these inhibitors singly or in combination to CHO-Pro5 cells did not alter levels of Ad5Luc1 gene transfer (FIG. 6B). In contrast, Ad5Luc1-PK gene transfer was blocked 35% by benzyl-α-GalNAc pre-treatment, with a minimal (<10%) reduction by swainsonine. Similar results were also observed in A549 cells pre-treated with these inhibitors, suggesting that O-linked cell-surface glycans may be preferred by Ad5Luc1-PK for infection. Collectively, these data show that the CBDs in the chimeric fiber protein of Ad5Luc1-PK directly participate in cellular attachment and that infection is highly dependent on the presence of lactose and/or N-acetyl-lactosamine-containing glycans, consistent with a novel, glycan-mediated cell entry pathway.

Example 4

This example illustrates enhanced infectivity of Ad5Luc1-PK in murine dendritic cells.

Figure 7:
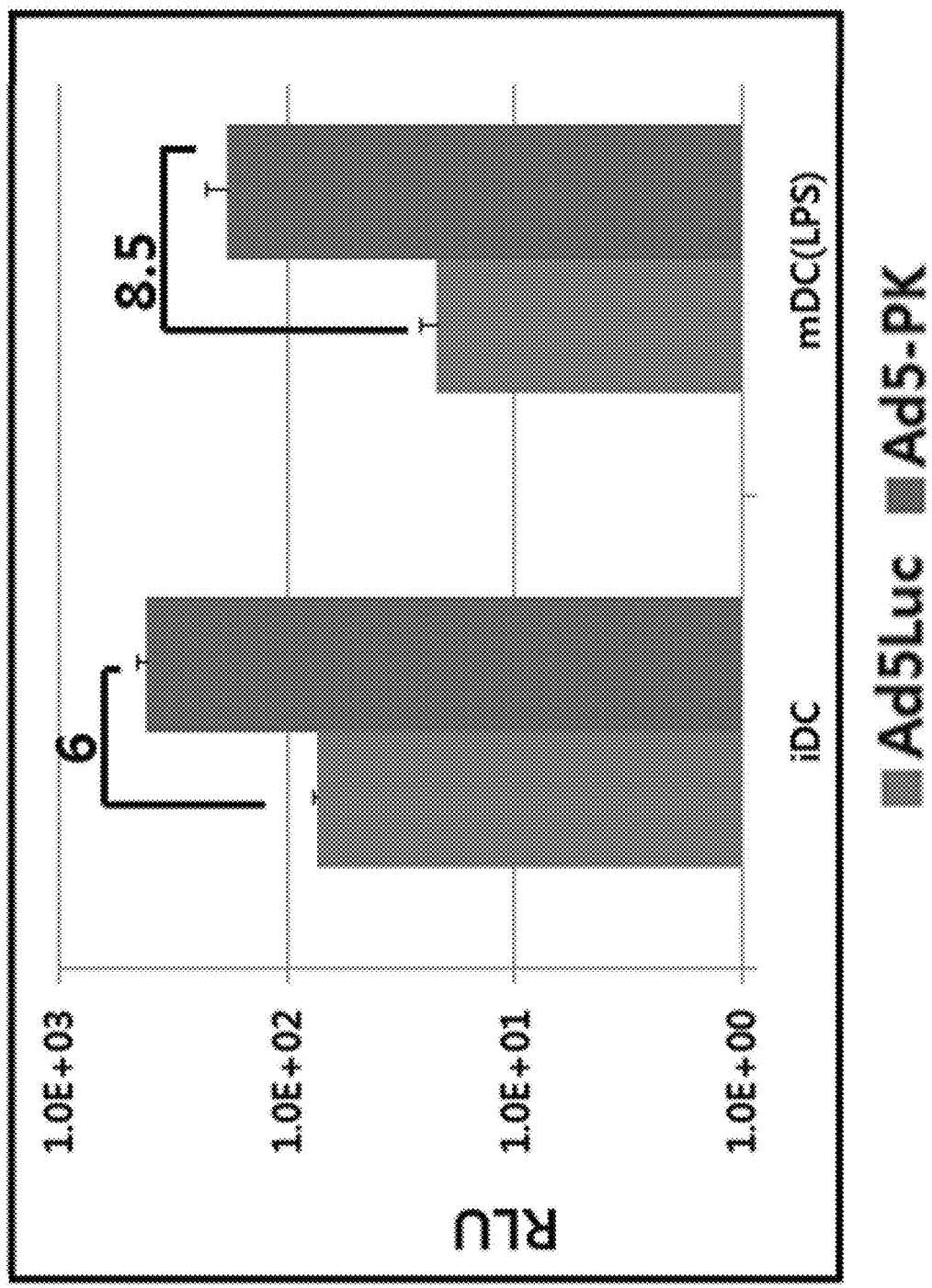
FIG. 7 illustrates Ad5Luc1-PK infectivity in murine dendritic cells.

To analyze infectivity of Ad5Luc1-PK, gene transfer assays were performed in immature (iDC) and mature (LPS-treated) (mDC) murine dendritic cells. In these experiments, iDC and mDC were infected with the Ad5Luc1 and Ad5Luc1-PK. Ad5Luc1-PK demonstrated a 6-fold increase in luciferase activity in iDC compared to Ad5Luc1, while in mDC Ad5Luc1-PK demonstrated a 8.5 fold increase in luciferase activity as compared to Ad5Luc1 (FIG. 7).

Example 5

This example illustrates enhanced infectivity of Ad5Luc1-PK in *Cynomolgus macaque* dendritic cells.

Figure 8:
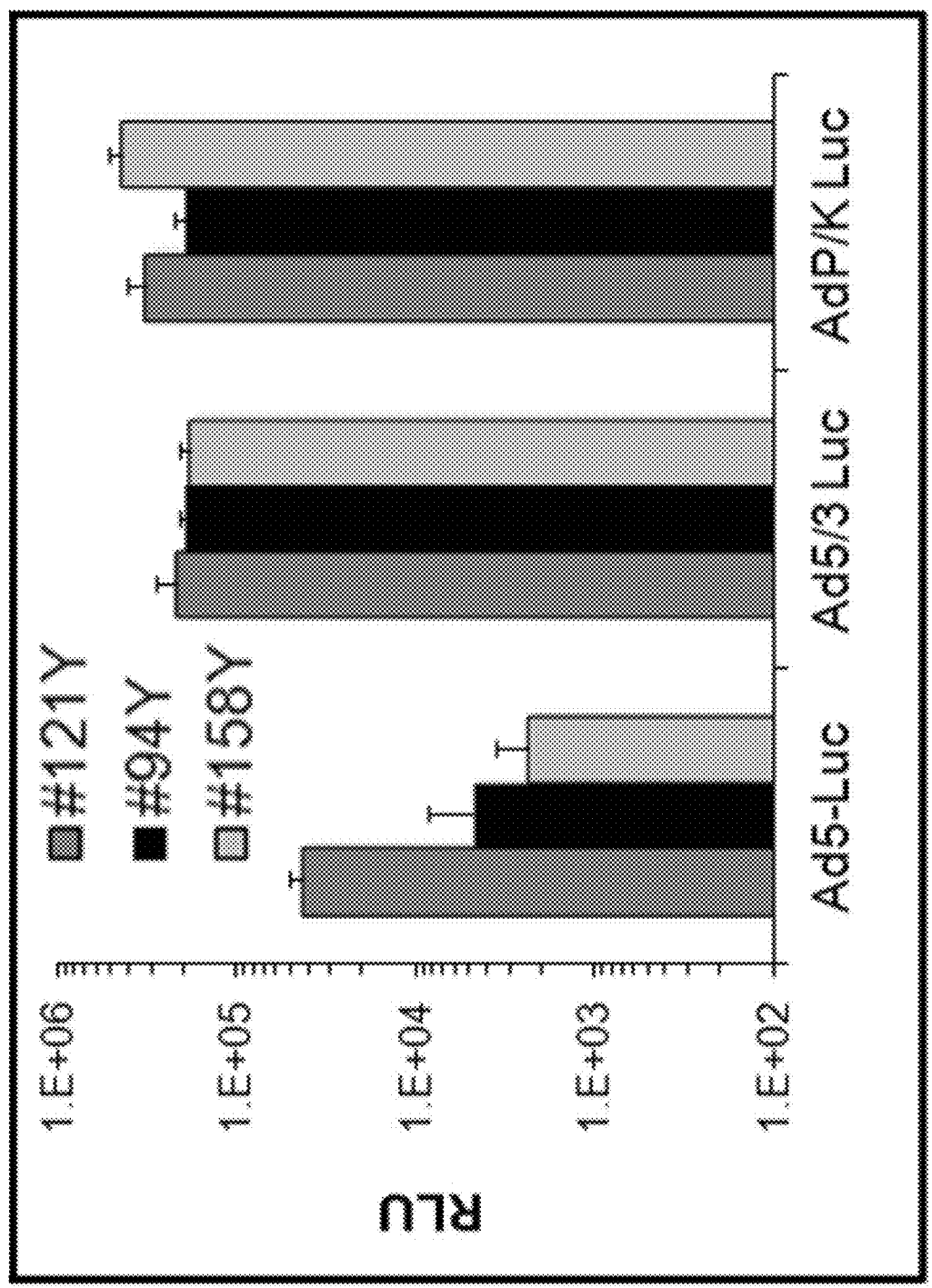
FIG. 8 illustrates Ad5Luc1-PK infectivity in *Cynomolgus macaque* dendritic cells.

To analyze infectivity of Ad5Luc1-PK in *Cynomolgus macaque* dendritic cells, gene transfer assays were performed in *C. macaque* dendritic cells. In these experiments, *C. macaque* dendritic cells were infected with Ad5Luc1, Ad5/3 and Ad5Luc1-PK. Ad5Luc1-PK demonstrated an increase in luciferase activity compared to Ad5/3 and Ad5Luc1 (FIG. 8). Ad5Luc1 (FIG. 7).

Example 6

This example illustrates enhanced infectivity of Ad5Luc1-PK in human dendritic cells.

Figure 9:
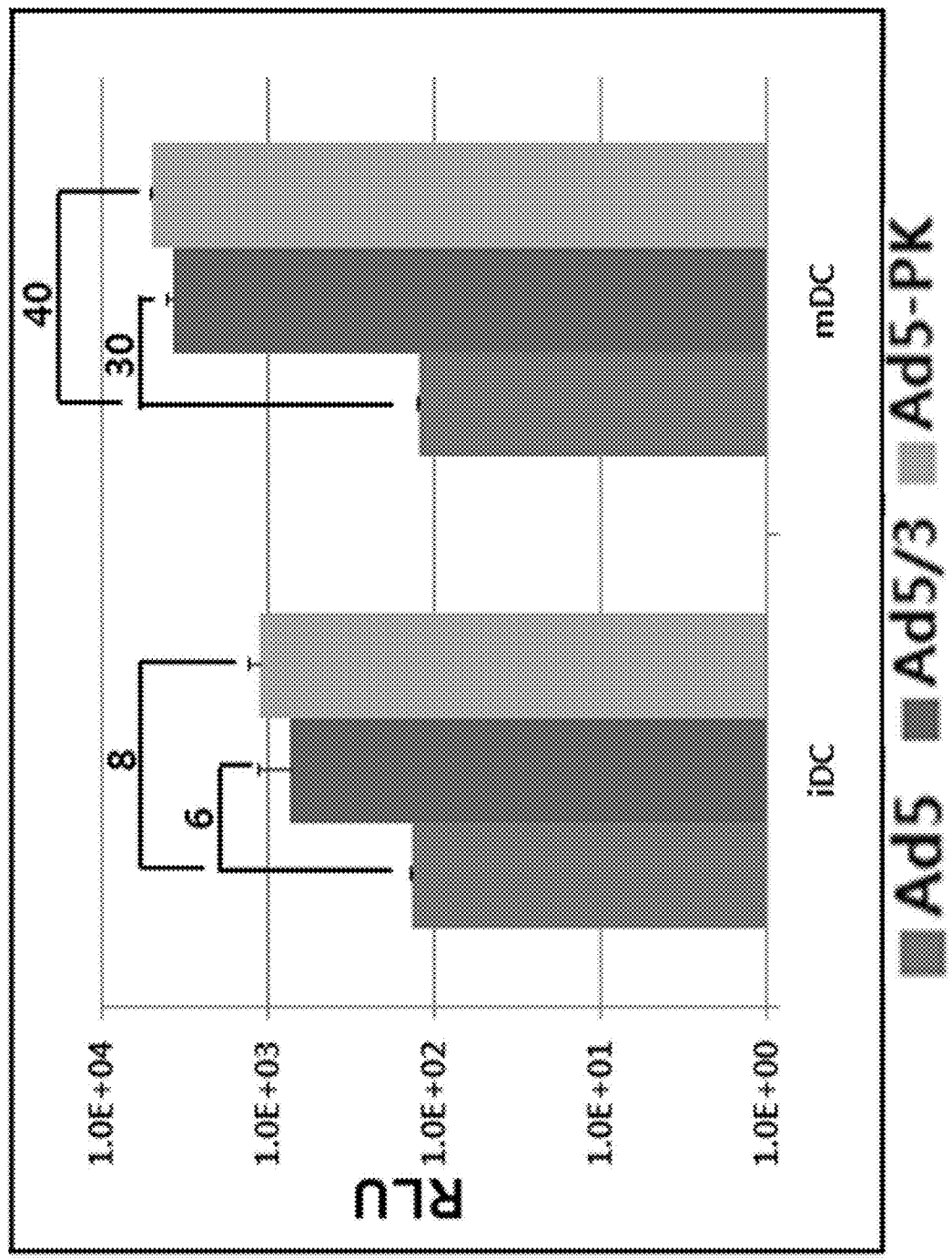
FIG. 9 illustrates Ad5Luc1-PK infectivity in human dendritic cells.

To analyze infectivity of Ad5Luc1-PK in human dendritic cells, gene transfer assays were performed in immature (iDC) and mature (mDC) human dendritic cells. In these experiments, human dendritic cells were infected with Ad5Luc1, Ad5/3 and Ad5Luc1-PK. In iDC, Ad5/3 demonstrated a 6-fold increase in luciferase activity as compared to Ad5Luc1, while in mDC, Ad5/3 demonstrated a 30-fold increase in luciferase activity as compared to Ad5Luc1 (FIG. 9). In iDC, Ad5Luc1-PK demonstrated an 8-fold increase in luciferase activity compared to Ad5Luc1, while in mDC, Ad5Luc1-PK demonstrated a 40-fold increase in luciferase activity compared to Ad5Luc1 (FIG. 9).

Example 7

This example illustrates FACS analysis of enhanced infectivity of Ad5GFP1-PK in immature human dendritic cells.

Figure 10:
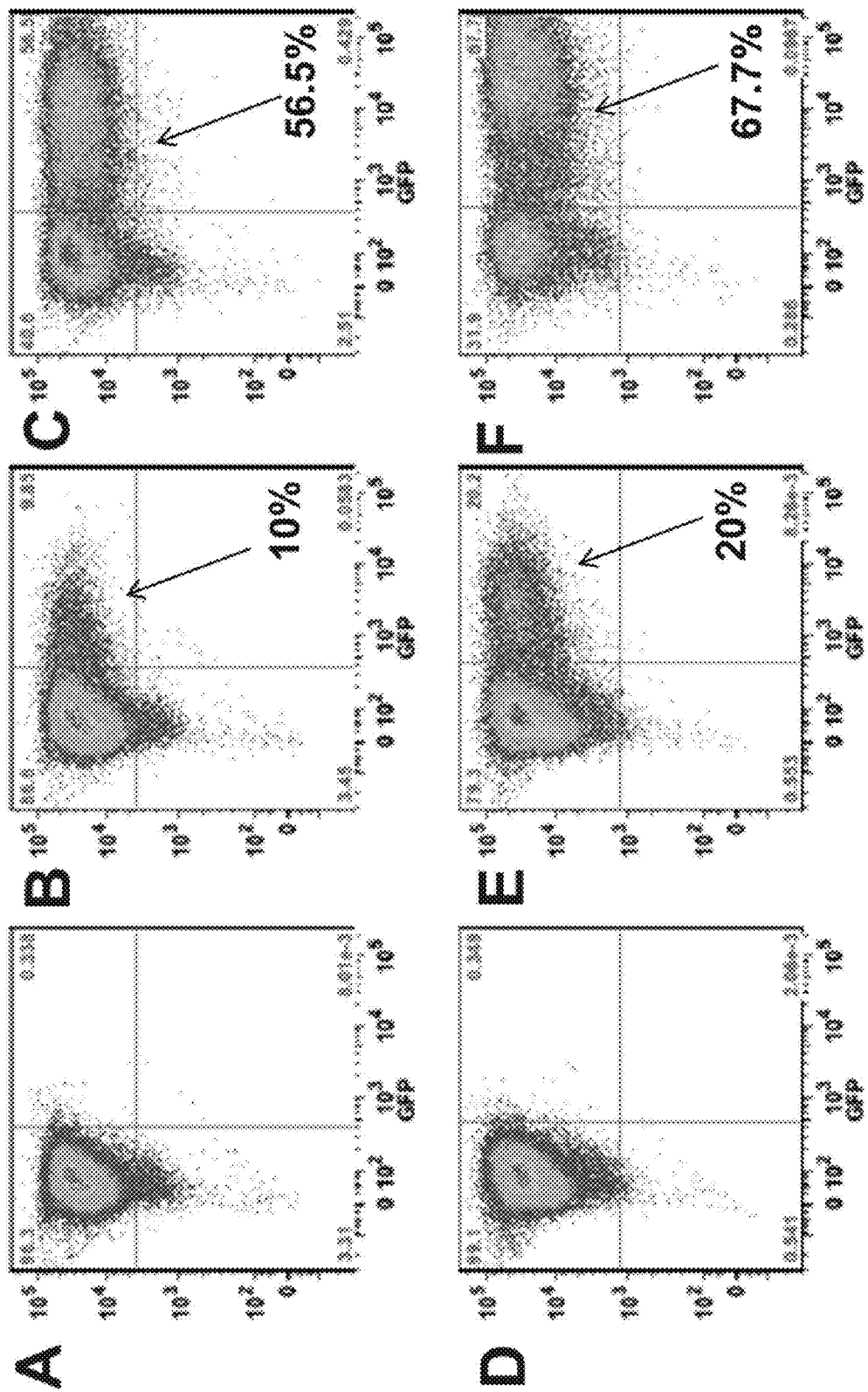
FIG. 10 illustrates Ad5GFP-PK infectivity in human dendritic cells.

To analyze infectivity of Ad5GFP1-PK, gene transfer assays were performed in human dendritic cells. In these experiments, immature human dendritic cells were infected with the Ad5GFP control vector (FIG. 10B, FIG. 10E) and Ad5GFP1-PK (FIG. 10C, FIG. 10F), a vector isogenic to Ad5Luc1-PK except that the firefly luciferase reporter gene was replaced with green fluorescent protein, GFP. Uninfected immature human dendritic cells are shown in FIG. 10A and FIG. 10D. Flow cytometry was performed using standard procedures at 24 (FIG. 10A, B, C) and 48 (FIG. 10D, E, F) hours after infection. After 24 hours of infection, Ad5GFP infected about 10% of the dendritic cell population (FIG. 10B) as compared to control (FIG. 10A), while Ad5GFP-PK infected 56.5% of the dendritic cell population (FIG. 10C) as compared to control (FIG. 10A). After 48 hours of infection, Ad5GFP infected about 20% of the dendritic cell population (FIG. 10E) as compared to control (FIG. 10D), while Ad5GFP-PK infected 67.7% of the dendritic cell population (FIG. 10F) as compared to control (FIG. 10D).

Example 8

This example illustrates that xeno-knob-modified adenovirus can have enhanced infectivity in human dendritic cells compared to other adenoviruses.

To analyze the efficiency of gene delivery of xenotype-modified adenoviral vectors on dendritic cell lines in vitro, five xeno-knob fiber-modified vectors can be used. In vectors Ad5Luc1-MK, Ad5Luc1-PK, Ad5Luc1-CK1 and Ad5Luc1-CK2 the native Ad5 fiber knob domain can be replaced by the corresponding fiber knob domain from mouse adenovirus type 1, porcine adenovirus, or canine adenovirus type 1 or 2, respectively. In the Ad5Luc1-OvF, the entire Ad5 fiber can be replaced with the fiber from ovine adenovirus 7. A control vector, Ad5Luc1 comprising the native Ad5 fiber, and a fiber-modified vector, Ad5/3, comprising a human Ad serotype 3 fiber knob domain can be used in this example. Both of these vectors can serve as controls to which other fiber-modified Ad vectors can be compared. All Ad vectors can be isogenic except for the fiber gene. The luciferase transgene activity of fiber-modified vectors can be compared to the Ad5Luc1 control vector in dendritic cell lines; plasmacytoid DCs, monocyte-derived DCs, migratory DCs, and lymphoid DCs. Luciferase expression levels can be shown as relative light units (RLU) normalized to that of Ad5Luc1 (Ad5Luc1=100%). Three of the vectors, Ad5Luc1-MK, Ad5Luc1-OvF, and Ad5Luc1-CK2 can augment gene delivery less than 2.5-fold above Ad5Luc1 in dendritic cell lines. In various dendritic cells, the Ad5Luc1-CK1 vector can provide an increase in luciferase transgene activity of at least 7-fold compared to an Ad5Luc1 control. In various dendritic cells, the Ad5Luc1-CK1 vector can provide an increase in luciferase transgene activity of up to 50-fold compared to an Ad5Luc1 control. The Ad5Luc1-PK vector can have an increase in gene delivery from 10-fold up to 20-fold above Ad5Luc1 in the dendritic cell lines. An Ad5/3 vector can enhance gene delivery 14-fold up to 50-fold in dendritic cell lines compared to an Ad5Luc1. Infectivity levels of these two viral vectors (comprising the porcine knob or the canine knob) in the four dendritic cell lines can be similar to or can exceed that of Ad5/3, which had previously been shown to act as a successful fiber-modified vector for enhancement of viral infectivity in human dendritic cells.

Example 9

This example demonstrates that xeno-knob modified infectivity can be independent of adenovirus native receptor, coxsackie-adenovirus-receptor (CAR).

To analyze the infectivity independent of CAR on dendritic cell lines in vitro, Ad5Luc1-PK and Ad5Luc1 can be used, where the Ad5Luc1 can be used as a control. The luciferase transgene activity of Ad5Luc1-PK vector can be compared to the Ad5Luc1 control vector in two dendritic cell lines, monocyte-derived DCs and monocyte-derived DCs that constitutively express high levels of CAR. The luciferase expression levels can be shown as relative light units (RLU). After infection of Ad5Luc, into two dendritic cell lines, the luciferase transgene activity can increase up to 60 fold in monocyte-derived DCs that constitutively express CAR when compared to monocyte-derived dendritic cells. After infection of Ad5Luc1-PK, into monocyte-derived DCs, the luciferase transgene activity can be more then 60-fold increase when compared to Ad5Luc luciferase transgene activity in monocyte-derived DCs. Furthermore, no increase in luciferase transgene activity could (would) be observed in monocyte-derived cells that constitutively express CAR infected with Ad5Luc1-PK, as compared to monocyte-derived DCs infected with Ad5Luc1-PK.

To further demonstrate that xeno-modified infectivity can be independent of CAR, an Ad5 Knob Inhibition assay can be performed. Monocyte-derived DCs that constitutively overexpress CAR can be infected with Ad5Luc or Ad5Luc1-PK where increasing amounts from 0-100 µg/ml of Ad5 Knob can be added to the infection mixture. The luciferase expression levels can be shown as relative light units (RLU). After infection of Ad5Luc into monocyte-derived DCs overexpressing CAR, there can be a 3-fold decrease in luciferase transgene activity when comparing infection with no Ad5 Knob present and infection with 10 µg/mL of Ad5 Knob present. Infection with 50 µg/mL or 100 µg/mL of Ad5 Knob present can further decrease the luciferase transgene activity. After infection of Ad5Luc1-PK into monocyte-derived DCs overexpressing CAR, there may be no effect on luciferase transgene activity when comparing infection with no Ad5 Knob present and infection with 10 µg/mL of Ad5 Knob present. Infection with increasing amounts of Ad5 Knob, such as 50 µg/mL or 100 µg/mL, may not affect luciferase transgene activity in DCs overexpressing CAR infected with Ad5Luc1-PK.

Example 10

This example demonstrates that the porcine knob can bind to lactose and N-acetyl-lactosamine units.

The affinity of porcine adenovirus knob domain for Lacto-N-neotetraose, 3-aminopropyl-lacto-N-neotetraose, 2-azido-ethyl-di(N-acetyl-lactosamine), and 2-aminoethyl-tri(N-acetyl-lactosamine) can be assessed by surface plasmon resonance experiments. The galectin can be bound to a sensor chip, and the oligosaccharides can be injected at various concentrations to monitor their binding to the galectin domain. Sensorgrams can be evaluated via steady-state analysis to yield the corresponding isotherms from which the dissociation constants can be calculated. Surface plasmon resonance response can be calculated in µRIU. Lacto-N-neotetraose binds weakly to the galectin domain with a dissociation constant of 193±9 µM; while 3-aminopropyl-lacto-N-neotetraose, 2-azidoethyl-di(N-acetyl-lactosamine), 2-aminoethyl-tri(N-acetyl-lactosamine) bind stronger to the galectin domain with dissociation constants of 303±4 µM, 309±9 µM, and 308±40 µM, respectively.

All references cited are incorporated by reference, each in its entirety.

What is claimed is:

1. A method of transforming a dendritic cell, the method comprising contacting the dendritic cell with a chimeric adenovirus-5 (Ad5) comprising:
    a fiber comprising a tail, a shaft and a knob, wherein the knob is a porcine knob; and
    a nucleic acid comprising a promoter operably linked to a heterologous sequence encoding an antigen peptide.

2. A method in accordance with claim 1, wherein the fiber tail is an Ad5 tail and the fiber shaft is an Ad5 shaft.

3. A method in accordance with claim 1, wherein the chimeric Ad5 binds the dendritic cell via a dendritic cell receptor other than a CAR receptor or an integrin receptor.

4. A method in accordance with claim 1, wherein the knob comprises a galectin domain.

5. A method in accordance with claim 4, wherein the galectin domain binds to carbohydrates comprising lactose and N-acetyl-lactosamine units.

6. A method in accordance with claim 4, wherein the galectin domain binds a carbohydrate structure selected from the group consisting of Galβ1-4GlcNAcβ1-3Galβ1-4GlcNAcβ1-3Galβ1-4GlcNAc [tri(Nacetyl-lactosamine)], GlcNAcα1-4Galβ1-4GlcNAcβ1-3Galβ1-4GlcNAcβ1-3Galβ1-4GlcNAc, Galβ1-4GlcNAcβ1-3Galβ1-4Glc (lacto-N-neotetraose), Galα1-4Galβ1-4GlcNAcβ1-3Galβ1-4Glc, Galβ1-4GlcNAcβ1-3Galβ1-3GlcNAc.

7. A method in accordance with claim 1, wherein cellular uptake by the dendritic cell of DNA of the chimeric Ad5 is enhanced in comparison to cellular uptake by a dendritic cell of DNA of a wild-type Ad5.

8. A method in accordance with claim 1, wherein cellular uptake by the dendritic cell of DNA of the chimeric Ad5 is enhanced in comparison to cellular uptake by a dendritic cell of DNA of an adenovirus comprising a knob comprising an RGD sequence.

9. A method in accordance with claim 1, wherein infectivity of the chimeric Ad5 comprising a porcine knob for the dendritic cell exceeds that of wild-type Ad5.

10. A method in accordance with claim 1, wherein infectivity of the chimeric Ad5 comprising a porcine knob for an immature dendritic cell exceeds that of wild-type Ad5 by at least 8 fold.

11. A method of transforming dendritic cells in a cell culture, the method comprising adding to a cell culture comprising dendritic cells, a chimeric adenovirus-5 (Ad5) comprising a) a fiber comprising a tail, a shaft and a knob, wherein the knob is a porcine knob; and b) a nucleic acid comprising a promoter operably linked to a heterologous sequence encoding an antigen peptide.

12. A method in accordance with claim 11, wherein cellular uptake by the dendritic cells of the nucleic acid comprising a promoter operably linked to a heterologous sequence is enhanced in comparison to cellular uptake of a nucleic acid comprising a promoter operably linked to a heterologous sequence by dendritic cells contacted with wild-type Ad5.

13. A method in accordance with claim 11, wherein infectivity of the chimeric Ad5 comprising a porcine knob for the dendritic cells exceeds that of wild-type Ad5.

14. A method in accordance with claim 11, wherein the heterologous sequence encoding an antigen peptide is expressed in the dendritic cells at a level exceeding that of dendritic cells infected with Ad5.

15. A dendritic cell comprising a chimeric adenovirus-5 (Ad5) viral genome, wherein said chimeric Ad5 genome encodes a) a fiber comprising a tail, a shaft and a knob, wherein the knob is a porcine knob; and b) a promoter operably linked to a heterologous sequence encoding an immunizing antigen.

16. An ex vivo cell culture comprising a dendritic cell of claim 15.

17. A vaccine comprising a dendritic cell of claim 15.

18. A vaccine in accordance with claim 17, wherein the immunizing antigen is a peptide comprising or consisting of a sequence selected from the group consisting of NLVPMVATV (SEQ ID NO: 1), GLCTLVAML (SEQ ID NO: 2), GILGFVFTL (SEQ ID NO: 3), IMDQVPFSV (SEQ ID NO: 4), YLEPGPVTV (SEQ ID NO: 5).

* * * * *